US012626377B2

(12) United States Patent
Yang et al.

(10) Patent No.: US 12,626,377 B2
(45) Date of Patent: May 12, 2026

(54) SYSTEMS AND METHODS FOR IMAGE REGISTRATION

(71) Applicant: SHANGHAI UNITED IMAGING HEALTHCARE CO., LTD., Shanghai (CN)

(72) Inventors: Hongcheng Yang, Shanghai (CN); Jonathan Maltz, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 539 days.

(21) Appl. No.: 18/163,238

(22) Filed: Feb. 1, 2023

(65) Prior Publication Data

US 2023/0169668 A1      Jun. 1, 2023

Related U.S. Application Data

(63) Continuation of application No. PCT/CN2020/110257, filed on Aug. 20, 2020.

(51) Int. Cl.
*G06T 7/33* (2017.01)
*G06T 7/00* (2017.01)
(Continued)

(52) U.S. Cl.
CPC ............ *G06T 7/337* (2017.01); *G06T 7/0014* (2013.01); *G06T 7/11* (2017.01); *G06T 7/174* (2017.01);
(Continued)

(58) Field of Classification Search
CPC ......... G06T 7/0014; G06T 7/11; G06T 7/174; G06T 7/248; G06T 7/337;
(Continued)

(56) References Cited

U.S. PATENT DOCUMENTS

| | | | |
|---|---|---|---|
| 6,240,218 B1 | 5/2001 | Michael et al. | |
| 8,818,105 B2 | 8/2014 | Myronenko et al. | |

(Continued)

FOREIGN PATENT DOCUMENTS

| | | |
|---|---|---|
| CN | 103679713 A | 3/2014 |
| CN | 103679736 A | 3/2014 |

(Continued)

OTHER PUBLICATIONS

Third Office Action in Chinese Application No. 202080104334.7 mailed on Jan. 21, 2025, 22 pages.
(Continued)

*Primary Examiner* — Jennifer Mehmood
*Assistant Examiner* — Jose M Torres
(74) *Attorney, Agent, or Firm* — METIS IP LLC

(57)          ABSTRACT

Systems and methods for image registration are provided. The method may include obtaining a reference image of an object (510); the object includes a target volume; determining a registration mask associated with a region of interest (ROI) based on the reference image (520), the ROI includes at least a portion of the target volume; obtaining a target image of the object (530); and performing an image registration on the reference image and the target image based on the registration mask (540).

20 Claims, 9 Drawing Sheets

600

(51) Int. Cl.

| | |
|---|---|
| *G06T 7/11* | (2017.01) |
| *G06T 7/174* | (2017.01) |
| *G06T 7/246* | (2017.01) |
| *G16H 30/40* | (2018.01) |

(52) U.S. Cl.

CPC ............. *G06T 7/248* (2017.01); *G16H 30/40* (2018.01); *G06T 2207/20021* (2013.01); *G06T 2207/30096* (2013.01)

(58) Field of Classification Search

CPC . G06T 2207/10124; G06T 2207/20021; G06T 2207/30004; G06T 2207/30096; G16H 30/40; A61N 5/1049; A61N 2005/1062

See application file for complete search history.

(56) References Cited

U.S. PATENT DOCUMENTS

| | | | |
|---|---|---|---|
| 2004/0218794 | A1 | 11/2004 | Kao et al. |
| 2005/0265453 | A1 | 12/2005 | Saito |
| 2009/0010540 | A1* | 1/2009 | Mullick .................... G06T 7/38 |
| | | | 382/170 |
| 2010/0128954 | A1 | 5/2010 | Ostrovsky-Berman et al. |
| 2013/0058555 | A1* | 3/2013 | Miao .................... G06V 20/653 |
| | | | 382/132 |
| 2015/0161789 | A1 | 6/2015 | Roujol et al. |
| 2015/0334398 | A1 | 11/2015 | Socek et al. |
| 2016/0371862 | A1 | 12/2016 | Silver et al. |
| 2017/0046837 | A1 | 2/2017 | Leinhard et al. |
| 2017/0161897 | A1 | 6/2017 | Hoffmann et al. |
| 2017/0249744 | A1* | 8/2017 | Wang ........................ G06T 1/60 |
| 2017/0337675 | A1 | 11/2017 | Gelman et al. |
| 2018/0197303 | A1 | 7/2018 | Jordan et al. |
| 2019/0073802 | A1 | 3/2019 | Case et al. |
| 2019/0205642 | A1 | 7/2019 | Cugnet et al. |
| 2019/0236816 | A1 | 8/2019 | Wang et al. |
| 2019/0295268 | A1 | 9/2019 | Gass et al. |
| 2020/0327684 | A1* | 10/2020 | Bose ......................... G06T 7/33 |
| 2020/0342602 | A1* | 10/2020 | Tanaka ..................... G06T 7/38 |

FOREIGN PATENT DOCUMENTS

| | | |
|---|---|---|
| CN | 107580217 A | 1/2018 |
| CN | 108563984 A | 9/2018 |
| CN | 109840881 A | 6/2019 |
| EP | 3420902 A1 | 1/2019 |

OTHER PUBLICATIONS

The Second Office Action in Chinese Application No. 202080104334.7 mailed on Sep. 27, 2024, 20 pages.

International Search Report in PCT/CN2020/110257 mailed on Apr. 27, 2021, 5 pages.

Written Opinion in PCT/CN2020/110257 mailed on Apr. 27, 2021, 3 pages.

Ren, Lei et al., Automatic Registration between Reference and On-Board Digital Tomosynthesis Images for Positioning Verification, Medical Physics, 35(2): 664-672, 2008.

Li, Guang et al., Clinical Assessment of 2D/3D Registration Accuracy in 4 Major Anatomic Sites Using On-Board 2D Kilovoltage Images for 6D Patient Setup, Technology in Cancer Research & Treatment, 14(3): 305-314, 2015.

Hanno Schumacher et al., Weighted Medical Image Registration with Automatic Mask Generation, Medical Imaging, SPIE Proceedings, 6144: 61442B-1-61442B-8, 2006.

Amelia Campbell et al., Evaluating the Accuracy of the XVI Dual Registration Tool Compared with Manual Soft Tissue Matching to Localise Tumour vols. for Post-Prostatectomy Patients Receiving Radiotherapy, Journal of Medical Imaging and Radiation, 59(4): 527-534, 2015.

* cited by examiner

200

Processor
210

Storage
220

I/O
230

Communication
Port
240

300

500

Obtaining a reference image of an object 510

Determining a registration mask associated with a region of interest (ROI) based on the reference image 520

Obtaining a target image of the object 530

Performing an image registration on the reference image and the target image based on the registration mask 540

<u>600</u>

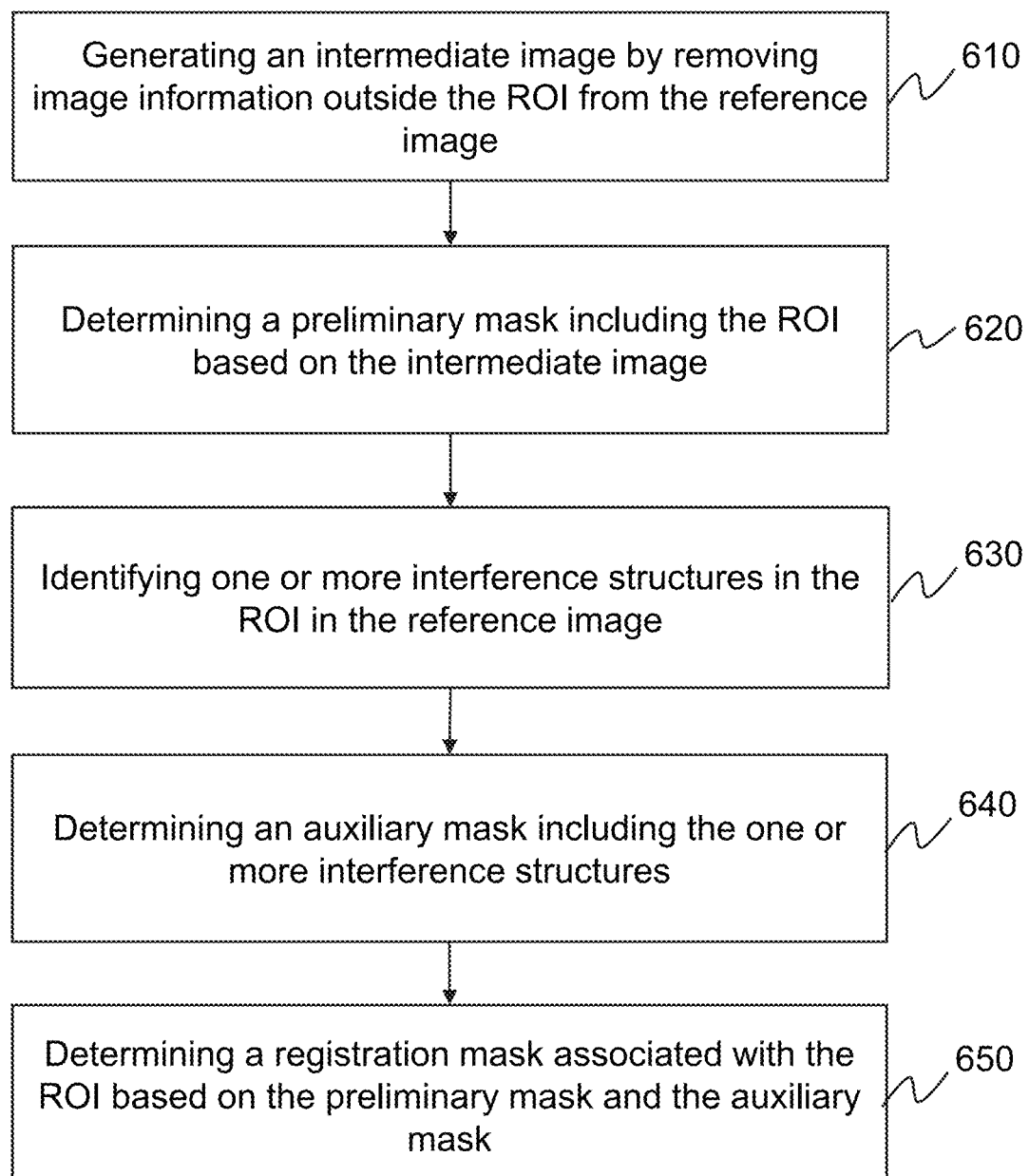

Generating an intermediate image by removing image information outside the ROI from the reference image — 610

Determining a preliminary mask including the ROI based on the intermediate image — 620

Identifying one or more interference structures in the ROI in the reference image — 630

Determining an auxiliary mask including the one or more interference structures — 640

Determining a registration mask associated with the ROI based on the preliminary mask and the auxiliary mask — 650

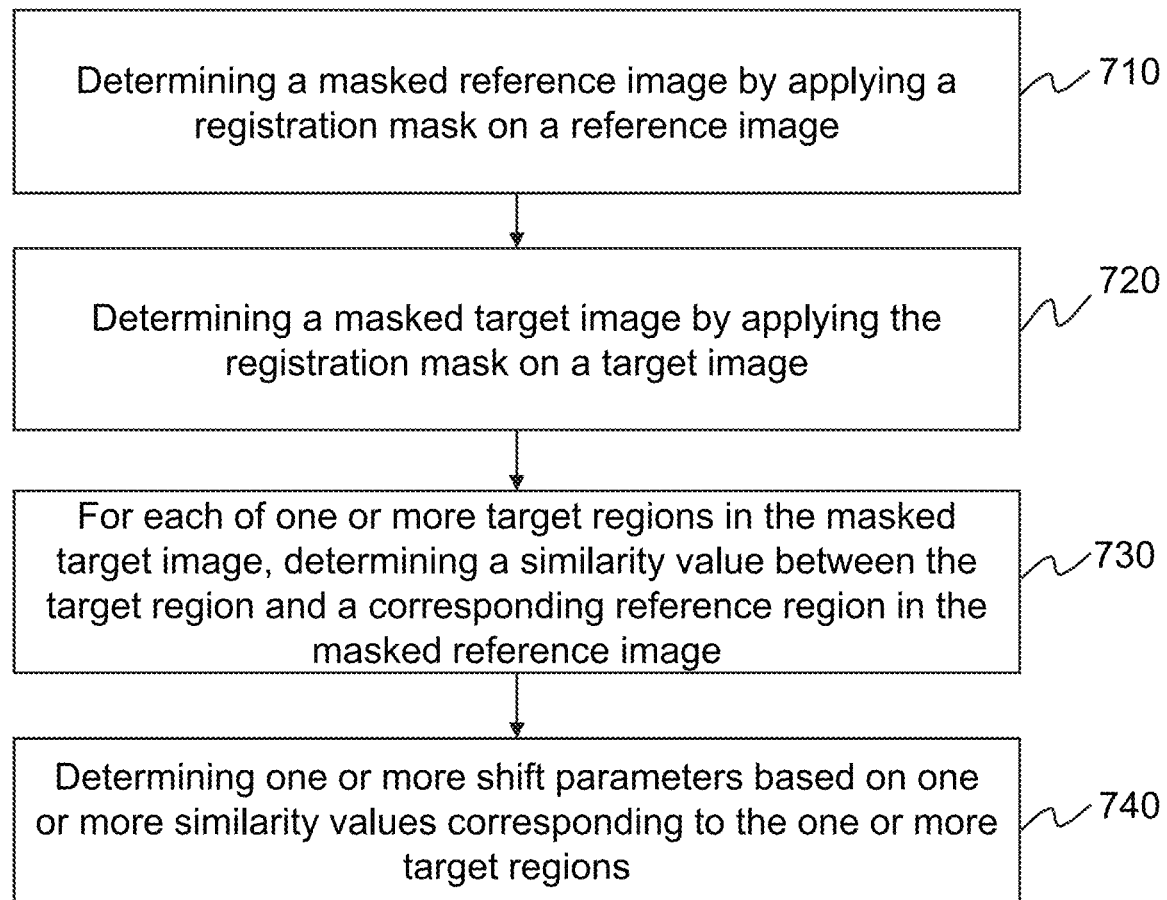

Determining a masked reference image by applying a registration mask on a reference image — 710

Determining a masked target image by applying the registration mask on a target image — 720

For each of one or more target regions in the masked target image, determining a similarity value between the target region and a corresponding reference region in the masked reference image — 730

Determining one or more shift parameters based on one or more similarity values corresponding to the one or more target regions — 740

FIG. 7

Image 1b    Image 2b

Image 3b    Image 4b

SYSTEMS AND METHODS FOR IMAGE REGISTRATION

CROSS-REFERENCE TO RELATED APPLICATIONS

This application is a continuation of International Patent Application No. PCT/CN2020/110257, filed on Aug. 20, 2020, the entire contents of which are hereby incorporated by reference.

TECHNICAL FIELD

The present disclosure generally relates to image processing, and more particularly, relates to systems and methods for image registration.

BACKGROUND

Image-guided radiation therapy (IGRT) is a form of radiation therapy that is widely used in clinical treatment for many types of cancers. During a radiation therapy process, a treatment image acquired before or during a radiation treatment often needs to be registered with a planning image generated in advance for planning the radiation treatment, so that the radiation treatment can be accurately delivered to a target volume (e.g., a tumor) of an object (e.g., a patient) according to the treatment plan. However, some interference features (e.g., a moving organ or tissue) may significantly affect a registration result between the treatment image and the planning image, which influences subsequent treatment and/or clinical diagnosis. Thus, it is desirable to develop systems and methods for image registration to remove or reduce the influence of the interference structures, thereby improving registration accuracy.

SUMMARY

According to an aspect of the present disclosure, a system for image registration is provided. The system may include at least one storage device storing executable instructions and at least one processor in communication with the at least one storage device. When executing the executable instructions, the at least one processor is configured to cause the system to perform operations. The operations may include obtaining a reference image of an object, the reference image including a target volume. The operations may further include determining a registration mask associated with a region of interest (ROI) based on the reference image, the ROI including at least a portion of the target volume. The operations may further include obtaining a target image of the object, the target image including the target volume. The operations may further include performing an image registration on the reference image and the target image based on the registration mask.

In some embodiments, to determine the registration mask associated with the ROI based on the reference image, the operations may include generating an intermediate image by removing image information outside the ROI from the reference image; and determining the registration mask associated with the ROI based on the intermediate image.

In some embodiments, to determine the registration mask associated with the ROI based on the intermediate image, the operations may include performing a filtering operation on the intermediate image; and determining the registration mask associated with the ROI based on the filtered intermediate image.

In some embodiments, to determine the registration mask associated with the ROI based on the reference image, the operations may include determining a preliminary mask including the ROI based on the reference image; identifying one or more interference structures at least partially located in the ROI in the reference image; determining an auxiliary mask including the one or more interference structures; and determining the registration mask associated with the ROI based on the preliminary mask and the auxiliary mask.

In some embodiments, to identify the one or more interference structures at least partially located in the ROI in the reference image, the operations may include automatically segmenting the one or more interference structures from the reference image based on a preset rule.

In some embodiments, the preset rule includes at least one of a structure type, a structure label, or time information associated with the reference image.

In some embodiments, the one or more interference structures may include at least one of a moving organ or a moving tissue.

In some embodiments, the moving organ or moving tissues are determined from cine reference images.

In some embodiments, the moving organ or moving tissues are determined from cine target images.

In some embodiments, the moving organ or moving tissues are determined from motion characteristics of organs or tissues identified in the target or reference images.

In some embodiments, the one or more interference structures include at least one of a heart, a lung, a diaphragm, a bladder, or a rectum.

In some embodiments, to perform the image registration on the reference image and the target image based on the registration mask, the operations may include determining a masked reference image by applying the registration mask on the reference image; determining a masked target image by applying the registration mask on the target image; and determining one or more shift parameters based on the masked reference image and the masked target image.

In some embodiments, to determine the one or more shift parameters based on the masked reference image and the masked target image, for each of one or more target regions in the masked target image, the operations may include determining a similarity value between the target region and a corresponding reference region in the masked reference image; and determining the one or more shift parameters based on one or more similarity values corresponding to the one or more target regions.

In some embodiments, the reference image and the target image are acquired at a same respiratory phase.

In some embodiments, the reference image is a planning image associated with a treatment; and the target image is a treatment image during the treatment.

In some embodiments, the planning image may be a digitally reconstructed radiograph (DRR), and the treatment image may be an X-ray image.

In some embodiments, each of the reference image and the target image is a 3D image or a 4D image.

According to another aspect of the present disclosure, a method for image registration is provided. The method may be implemented on a computing device having at least one processor and at least one storage device. The method may include obtaining a reference image of an object, the reference image including a target volume; determining a registration mask associated with a region of interest (ROI) based on the reference image, the ROI including at least a portion of the target volume; obtaining a target image of the object, the target image including the target volume; and performing an image registration on the reference image and the target image based on the registration mask.

According to yet another aspect of the present disclosure, a non-transitory computer readable medium is provided, comprising at least one set of instructions, wherein when executed by at least one processor of a computing device, the at least one set of instructions direct the at least one processor to perform a method. The method may include obtaining a reference image of an object, the reference image including a target volume; determining a registration mask associated with a region of interest (ROI) based on the reference image, the ROI including at least a portion of the target volume; obtaining a target image of the object, the target image including the target volume; and performing an image registration on the reference image and the target image based on the registration mask.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 is a flowchart illustrating an exemplary process for determining a registration mask according to some embodiments of the present disclosure;

FIG. 7 is a flowchart illustrating an exemplary process for registering a reference image with a target image based on a registration mask according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different levels in ascending order. However, the terms may be displaced by another expression if they achieve the same purpose.

Figure 2:
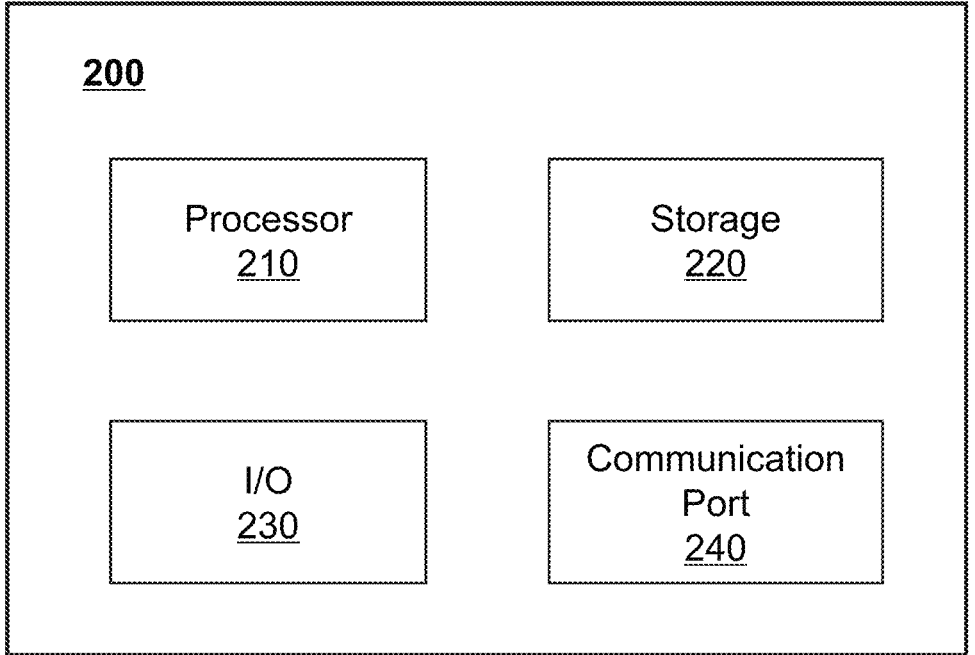
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "region," "location," and "area" in the present disclosure may refer to a location of an anatomical structure shown in the image or an actual location of the anatomical structure existing in or on a target subject's body, since the image may indicate the actual location of a certain anatomical structure existing in or on the target subject's body.

Provided herein are systems and methods for non-invasive biomedical imaging/treatment, such as for disease diagnostic, disease therapy, or research purposes. In some embodiments, the systems may include an imaging system. The imaging system may include a single modality system and/or a multi-modality system. The term "modality" used herein broadly refers to an imaging or treatment method or technology that gathers, generates, processes, and/or analyzes imaging information of a subject or treatments the subject. The single modality system may include, for example, an ultrasound imaging system, an X-ray imaging system, a computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near-infrared spectroscopy (NIRS) imaging system, or the like, or any combination thereof. The multi-modality system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a positron emission tomography-magnetic resonance imaging (PET-MR) system, a digital subtraction angiography-magnetic resonance imaging (DSA-MRI) system, etc. In some embodiments, the medical system may include a treatment system. The treatment system may include a treatment plan system (TPS), image-guided radiotherapy (IGRT), etc. The image-guide radiotherapy (IGRT) may include a treatment device and an imaging device. The treatment device may include a linear accelerator, a cyclotron, a synchrotron, etc., configured to perform a radio therapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc. It should be noted that the medical system described below is merely provided for illustration purposes, and not intended to limit the scope of the present disclosure.

In the present disclosure, the subject may include a biological object and/or a non-biological object. The biological subject may be a human being, an animal, a plant, or a specific portion, organ, and/or tissue thereof. For example, the subject may include a head, a neck, a thorax, a heart, a stomach, a blood vessel, a soft tissue, a tumor, a nodule, or the like, or any combination thereof. In some embodiments, the subject may be a man-made composition of organic and/or inorganic matters that are with or without life. The term "object" or "subject" are used interchangeably in the present disclosure.

In the present disclosure, a representation of an object (e.g., a patient, a subject, or a portion thereof) in an image may be referred to as "object" for brevity. For instance, a representation of an organ or tissue (e.g., a heart, a liver, a lung) in an image may be referred to as an organ or tissue for brevity. Further, an image including a representation of an object may be referred to as an image of an object or an image including an object for brevity. Still further, an operation performed on a representation of an object in an image may be referred to as an operation performed on an object for brevity. For instance, a segmentation of a portion of an image including a representation of an organ or tissue from the image may be referred to as a segmentation of an organ or tissue for brevity.

An aspect of the present disclosure relates to systems and methods for image registration. For example, the system may obtain a reference image of an object including a target volume. The system may further determine a registration mask associated with a region of interest (ROI) based on the reference image. The ROI may include at least a portion of the target volume. The system may also obtain a target image of the object including the target volume. The system may further perform an image registration on the reference image and the target image based on the registration mask. Accordingly, the system may register the reference image with the target image according to a region (i.e., the ROI including at least a portion of the target volume) that has clinical relevance to the target volume, which may improve the accuracy of image registration.

In some embodiments, one or more interference structures (e.g., a moving organ or tissue) may be excluded from the ROI to improve the registration accuracy. For example, an auxiliary mask including the one or more interference structures may be determined and used to exclude the one or more interference structures during the image registration. Accordingly, the registration accuracy can be efficiently improved, and the efficiency and/or accuracy of diagnosis and/or treatment performed based thereon can be efficiently improved.

Figure 1:
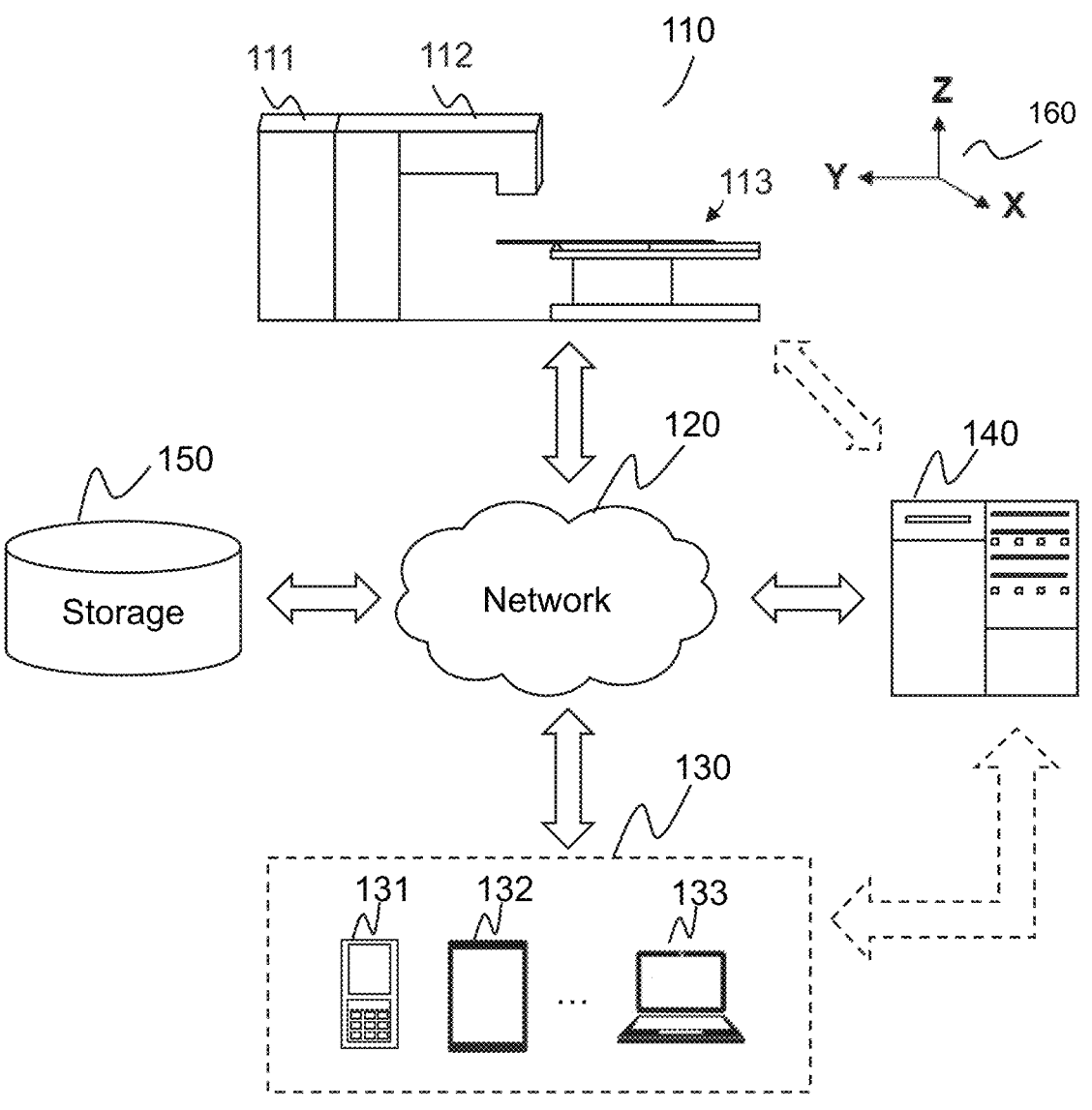
FIG. 1 is a schematic diagram illustrating an exemplary medical system according to some embodiments of the present disclosure.

FIG. 1 is a schematic diagram illustrating an exemplary medical system according to some embodiments of the present disclosure. As shown in FIG. 1, the medical system 100 may include a medical device 110, a network 120, a terminal device 130, a processing device 140, and a storage device 150. In some embodiments, two or more components of the medical system 100 may be connected to and/or communicate with each other via a wireless connection (e.g., the network 120), a wired connection, or a combination thereof. The components of the medical system 100 may be connected in various ways. Merely by way of example, the medical device 110 may be connected to the processing device 140 through the network 120 or directly. As another example, the storage device 150 may be connected to the processing device 140 through the network 120 or directly.

The medical device 110 may be configured to acquire image data of a subject and/or perform a treatment on the subject. For illustration purposes, a medical device with both image acquisition function and treatment function is described as an example. Accordingly, the medical device 110 may include an imaging device 111, a treatment device 112, and a table 113.

The imaging device 111 may be configured to acquire an image of a subject prior to a radiation treatment, during the radiation treatment, and/or after the radiation treatment. In some embodiments, the imaging device 111 may include a computed tomography (CT) device (e.g., a cone beam computed tomography (CBCT) device, a fan-beam computed tomography (FBCT) device), an ultrasound imaging device, a fluoroscopy imaging device, a magnetic resonance imaging (MRI) device, a single photon emission computed tomography (SPECT) device, a positron emission tomography (PET) device, an X-ray imaging device, or the like, or any combination thereof. For illustration purposes, the present disclosure takes a CT device as an exemplary imaging device 111.

In some embodiments, the imaging device 111 may include an imaging radiation source, a detector, and a gantry. The imaging radiation source and the detector may be mounted on the gantry. The imaging radiation source may emit radioactive rays to the subject. The detector may detect radiation events (e.g., x-ray photons, gamma-ray photons) emitted from an imaging region of the imaging device 111. In some embodiments, the detector may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

The treatment device 112 may be configured to deliver a radiotherapy treatment to the subject. In some embodiments, the treatment device 112 may include a treatment radiation source, a gantry, and a collimator. The treatment radiation source may be configured to emit treatment radiation towards the subject. In some embodiments, the treatment radiation source may include a linear accelerator (LINAC). The collimator may be configured to control the shape of the treatment radiations generated by the treatment radiation source.

In some embodiments, the imaging device 111 may be spaced by a distance from the treatment device 112. In some embodiments, the gantry of the imaging device 111 and the gantry of the treatment device 112 may share an axis of rotation. The subject may be positioned in different positions on the table 113 for imaging and treatment. In some embodiments, the imaging radiation source and the treatment radiation source may be integrated as a single radiation source to image and/or treat the subject. In some embodiments, the imaging device 111 and the treatment device 112 may share a same gantry. For example, the treatment radiation source may be mounted on the gantry of the imaging device 111. A subject may be placed on the table 113 for treatment and/or imaging. In some embodiments, the table 113 may be movable between the treatment device 112 and the imaging device 111 along a certain direction (e.g., a Y-axis direction of a coordinate system 160 as shown in FIG. 1).

The network 120 may include any suitable network that can facilitate the exchange of information and/or data for the medical system 100. In some embodiments, one or more components (e.g., the medical device 110, the processing device 140, the storage device 150, or the terminal device 130) of the medical system 100 may communicate information and/or data with one or more other components of the medical system 100 via the network 120. For example, the processing device 140 may obtain image data from the medical device 110 via the network 120. As another example, the processing device 140 may obtain user instruction(s) from the terminal device 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the medical system 100 may be connected to the network 120 to exchange data and/or information.

The terminal device 130 may be connected to and/or communicate with the medical device 110, the processing device 140, and/or the storage device 150. For example, the terminal device 130 may obtain a reference image including a region of interest (ROI) from the processing device 140. As another example, the terminal device 130 may enable user interactions with the medical system 100. In some embodiments, the terminal device 130 may include a mobile device 131, a tablet computer 132, a laptop computer 133, or the like, or any combination thereof. The mobile device 131 may include a mobile phone, a personal digital assistant (PDA), a gaming device, a navigation device, a point of sale (POS) device, a laptop, a tablet computer, a desktop, or the like, or any combination thereof. In some embodiments, the terminal device 130 may include an input device, an output device, etc. The input device may include alphanumeric and other keys that may be input via a keyboard, a touch screen (e.g., with haptics or tactile feedback), a speech input, an eye-tracking input, a brain monitoring system, or any other comparable input mechanism. The input information received through the input device may be transmitted to the processing device 140 via, for example, a bus, for further processing. Other types of input device may include a cursor control device, such as a mouse, a trackball, or cursor direction keys, etc. The output device may include a display, a speaker, a printer, or the like, or a combination thereof. In some embodiments, the terminal device 130 may be part of the processing device 140.

The processing device 140 may process data and/or information obtained from the medical device 110, the storage device 150, the terminal device 130, or other components of the medical system 100. For example, the processing device 140 may register a reference image with a target image based on a registration mark. As another example, the processing device 140 may remove one or more interference structures from the reference image and generate an auxiliary mask. Then the processing device 140 may generate the registration mask based on the auxiliary mask. In some embodiments, the processing device 120 may include a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local to or remote from the medical system 100. For example, the processing device 140 may access information and/or data from the medical device 110, the storage device 150, and/or the terminal device 130 via the network 120. As another example, the processing device 140 may be directly connected to the medical device 110, the terminal device 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, and inter-cloud, a multi-cloud, or the like, or a combination thereof. In some embodiments, the processing device 140 may be implemented by a computing device 200 having one or more components as described in connection with FIG. 2.

The storage device 150 may store data, instructions, and/or any other information. In some embodiments, the storage device 150 may store data obtained from the processing device 140, the terminal device 130, and/or the storage device 150. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components (e.g., the processing device 140, the terminal device 130) of the medical system 100. One or more components of the medical system 100 may access the data or instructions stored in the storage device 150 via the network 120. In some embodiments, the storage device 150 may be part of the processing device 140.

In some embodiments, a coordinate system 160 may be provided in the medical system 100 as illustrated in FIG. 1. The coordinate system 160 may include an X-axis, a Y-axis, and a Z-axis. The X-axis and the Y-axis shown in FIG. 1 may be horizontal, and the Z-axis may be vertical. As illustrated, the X-axis may be parallel to a lateral direction of the table 113, the Y-axis may be parallel to a longitudinal direction of the table 113, and the Z-axis may be parallel to a vertical direction of the table 113. The origin of the coordinate system 160 may be located at any suitable position. For example, the origin may be located at the isocenter of the LINAC of the treatment device 112, and the coordinate system 160 may be referred to as an RT coordinate system. As another example, the imaging device 111 may be a CT device. The origin of the coordinate system 160 may be located at the rotation center of the gantry of the CT device, and the coordinate system 160 may be referred to as a CT coordinate system. In some embodiments, the origin of the coordinate system 160 may be determined by an operator. In some embodiments, the origin of the coordinate system 160 may be determined by a default setting of the medical system 100.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure.

FIG. 2 is a schematic diagram illustrating exemplary hardware and/or software components of an exemplary computing device according to some embodiments of the present disclosure. In some embodiments, the processing device 140 may be implemented on the computing device 200. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the medical device 110, the terminal device 130, the storage device 150, and/or any other component of the medical system 100. In some embodiments, the processor 210 may include one or more hardware processors, such as a microcontroller, a microprocessor, a reduced instruction set computer (RISC), an application-specific integrated circuit (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, and thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the medical device 110, the terminal device 130, the storage device 150, and/or any other component of the medical system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 140 for determining a registration mask based on a reference image of a subject.

The I/O 230 may input and/or output signals, data, information, etc. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the medical device 110, the terminal device 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
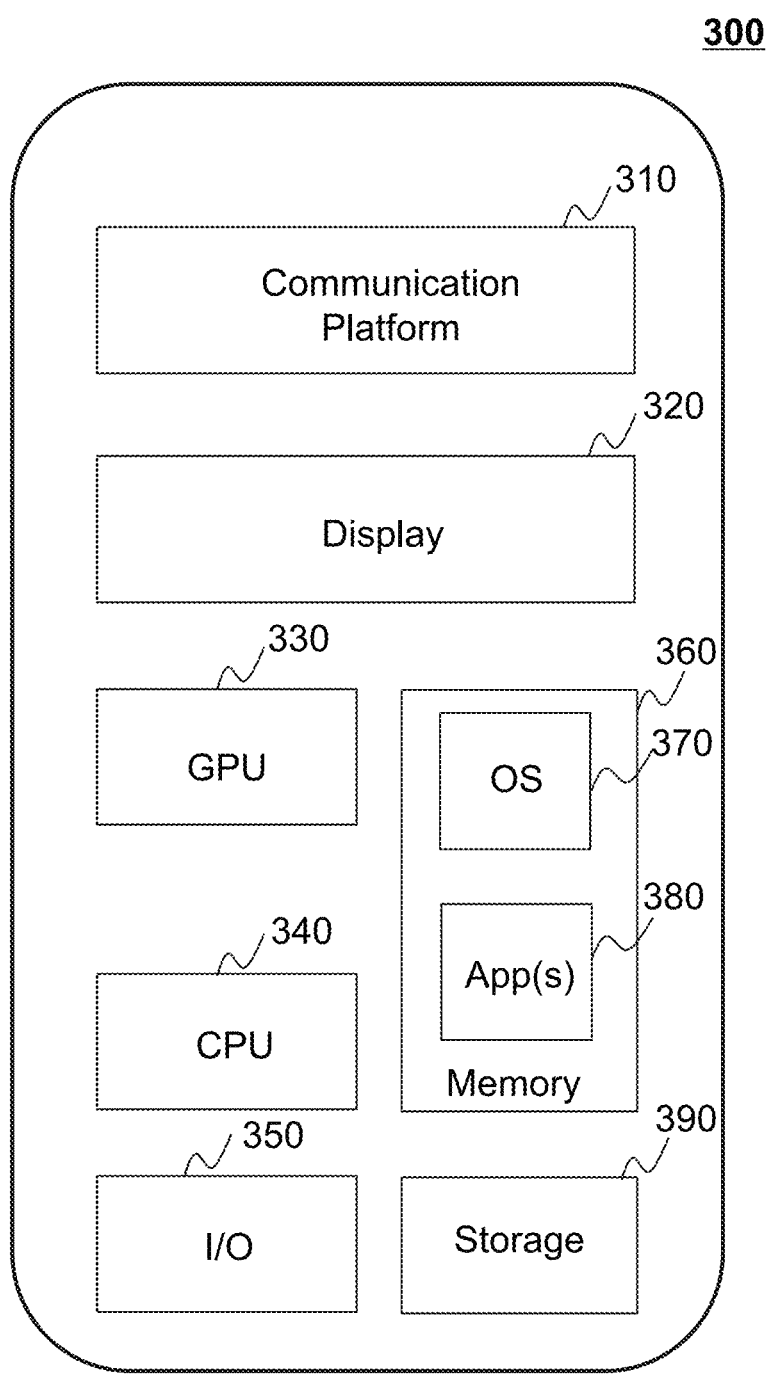
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, one or more components (e.g., the terminal device 130 and/or the processing device 140) of the medical system 100 may be implemented on the mobile device 300.

As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the medical system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
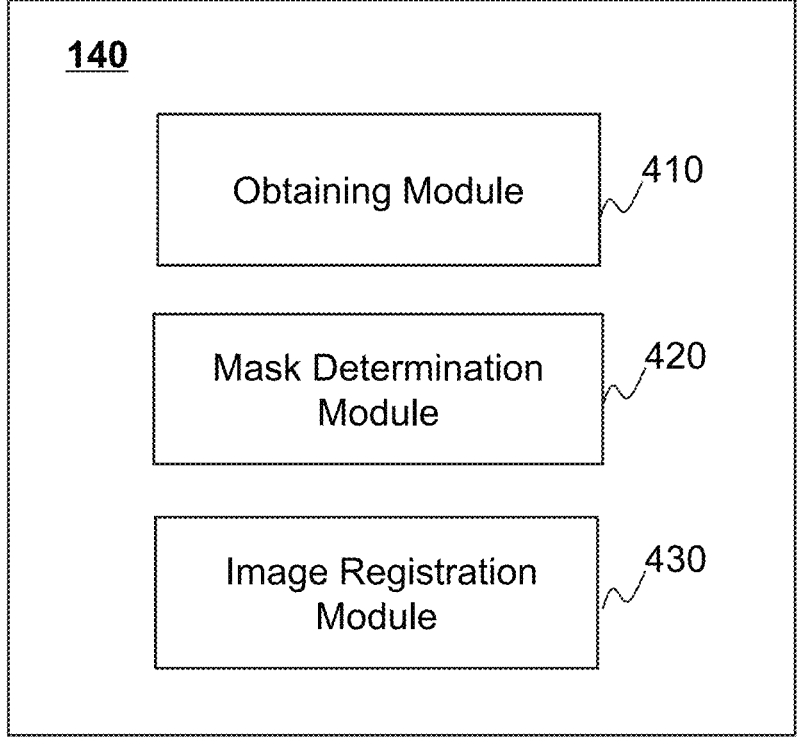
FIG. 4 is a block diagram illustrating an exemplary processing device according to some embodiments of the present disclosure.

FIG. 4 is a block diagram illustrating an exemplary processing device according to some embodiments of the present disclosure. As illustrated in FIG. 4, the processing device 140 may include an obtaining module 410, a mask determination module 420, and an image registration module 430. The modules may be hardware circuits of all or part of the processing device 140. The modules may also be implemented as an application or set of instructions read and executed by the processing device 140. Further, the modules may be any combination of the hardware circuits and the application/instructions. For example, the modules may be part of the processing device 140 when the processing device 140 is executing the application/set of instructions.

The obtaining module 410 may be configured to obtain information and/or data from one or more components of the medical system 100. For example, the obtaining module 410 may obtain a reference image (e.g., a DRR) and a target image (e.g., an X-ray image) of an object, wherein the reference image and the target image are generated at different time points.

The mask determination module 420 may be configured to determine a registration mask associated with an ROI based on the reference image. For example, the mask determination module 420 may generate an intermediate image by removing image information outside the ROI from the reference image, and then perform a filtering operation on the intermediate image. The mask determination module 420 may determine the registration mask associated with the ROI based on the filtered intermediate image. As another example, the mask determination module 420 may determine a preliminary mask including the ROI based on the reference image. The mask determination module 420 may identify one or more interference structures at least partially located in the ROI in the reference image. The mask determination module 420 may determine an auxiliary mask including the one or more interference structures, and then determine the registration mask associated with the ROI based on the preliminary mask and the auxiliary mask.

The image registration module 430 may be configured to perform an image registration on the reference image and the target image based on the registration mask. In some embodiments, the image registration module 430 may determine a masked reference image by applying the registration mask on the reference image, and a masked target image by applying the registration mask on the target image. The image registration module 430 may determine one or more shift parameters based on the masked reference image and the masked target image. For example, for each of one or more target regions in the masked target image, the image registration module 430 may determine a similarity value between the target region and a corresponding reference region in the masked reference image. The image registration module 430 may determine the one or more shift parameters based on one or more similarity values corresponding to the one or more target regions.

The modules in the processing device 140 may be connected to or communicated with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined into a single module, and any one of the modules may be divided into two or more units. For example, the obtaining module 410 may be divided into two units configured to obtain a reference image of an object and obtain a target image of the object respectively. As another example, the processing device 140 may further include a control module configured to generate control signals for one or more components in the medical system 100.

Figure 5:
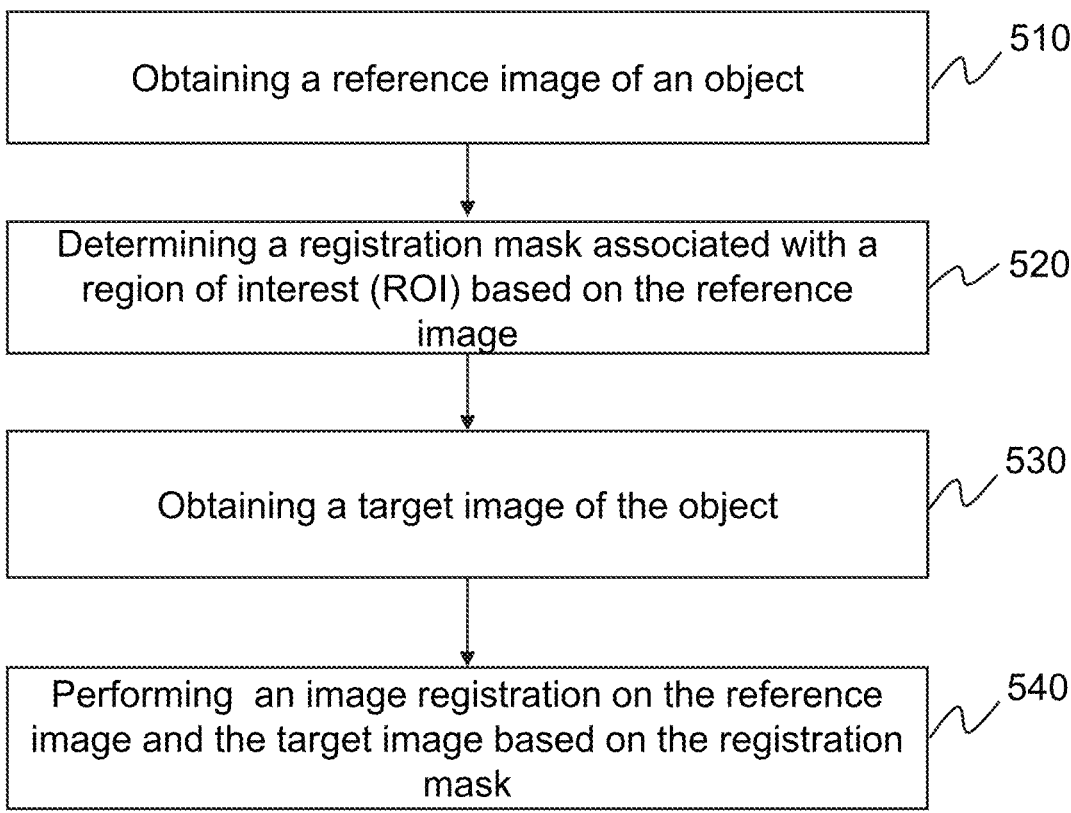
FIG. 5 is a flowchart illustrating an exemplary process for image registration according to some embodiments of the present disclosure.

FIG. 5 is a flowchart illustrating an exemplary process for image registration according to some embodiments of the present disclosure. In some embodiments, process 500 may be implemented as a set of instructions (e.g., an application) stored in the storage device 150, storage 220, or storage 390. The processing device 140, the processor 210, and/or the CPU 340 may execute the set of instructions, and when executing the instructions, the processing device 140, the processor 210, and/or the CPU 340 may be configured to perform the process 500. The operations of the illustrated process presented below are intended to be illustrative. In some embodiments, the process 500 may be accomplished with one or more additional operations not described, and/or without one or more of the operations discussed. Additionally, the order of the operations of the process 500 illustrated in FIG. 5 and described below is not intended to be limiting.

In 510, the processing device 140 (e.g., the obtaining module 410) may obtain a reference image of an object.

The reference image may include a target volume of the object. For example, the object may be a biological object (e.g., a patient, an animal) or a non-biological object (e.g., a phantom). Accordingly, the target volume of the object may include an organ, a tissue, or a specific portion of the object. Merely by way of example, the target volume may include a tumor, a lesion, etc. In some embodiments, the target volume may include a gross target volume (GTV), a clinical target volume (CTV), an internal target volume (ITV), a planning target volume (PTV), a treated volume (TV), an irradiated volume (IV), or the like, or a combination thereof. In some embodiments, the target volume may be a 2D region, a 3D region, a 4D region, etc.

In some embodiments, the processing device 140 may obtain the reference image from the medical device 110 (e.g., the imaging device 111), the storage device 150, or any other external device. For example, the imaging device 111 may transmit acquired reference imaging data (e.g., projection data) of the object to the storage device 150 for storage. The processing device 140 may obtain the reference imaging data from the storage device 150 and generate the reference image based on the reference imaging data. As another example, the processing device 140 may obtain the reference image from the storage device 150 directly.

In some embodiments, the reference image may be a two-dimensional (2D) image, a three-dimensional (3D) image, a four-dimensional (4D) image (e.g., a temporal series of 3D images), etc. In some embodiments, the reference image may be a planning image related to a radiation treatment. For example, the reference image may be a 3D scan image (e.g., a 3D CT image) of the object which is determined based on scanning data of the object obtained before the radiation treatment. As another example, the reference image may be a digitally reconstructed radiograph (DRR) generated from the 3D scan image (e.g., a DRR generated by projecting the 3D scan image onto an image plane) of the object or determined based on the scanning data of the object.

In 520, the processing device 140 (e.g., the mask determination module 420) may determine a registration mask associated with a region of interest (ROI) based on the reference image. The ROI may include at least a portion of the target volume. As used herein, the registration mask may be used to determine a registration processing area (e.g., an area corresponding to the ROI) in images to be registered during an image registration process.

In some embodiments, the ROI may be determined according to a default setting of the medical system 100 or determined by a user (e.g., an operator) via, for example, the terminal device 130 or an interface of the processing device 140. For example, the user may define a contour (e.g., a rectangular frame) enclosing at least a portion of the target volume via the terminal device 130. The processing device 140 may determine a region corresponding to the contour as the ROI. As another example, the processing device 140 may directly determine a region including at least a portion of the target volume as the ROI.

In some embodiments, the registration mask can be considered as a "registration mask image" which includes pixels (or voxels) with specified values (e.g., 0 or 1). For example, the registration mask may be a binary image including pixels (or voxels) corresponding to the ROI with values "1" and pixels (or voxels) corresponding to regions outside the ROI with values "0."

In some embodiments, the dimension of the reference image and that of the registration mask image may be the same or different. For example, both the dimension of the reference image and that of the registration mask image may be 2D. As another example, the dimension of the reference image may be 3D and that of the registration mask image may be 2D or 3D. For instance, the processing device 140 may generate a 3D registration mask image based on the 3D reference image and/or generate a 2D registration mask by projecting the 3D registration mask onto a predetermined plane.

In some embodiments, the processing device 140 may determine the registration mask based on one or more structures (e.g., an organ, a tissue) in the reference image, wherein the structures may be identified by the processing device 140 or may be pre-segmented in advance (e.g., the structures may be pre-segmented and included in a treatment plan for the radiation treatment). For example, the processing device 140 may classify the one or more structures into an inclusion set or an exclusion set. The inclusion set may include structure(s) (e.g., the target volume) located in the ROI; the exclusion set may include structure(s) located outside the ROI and/or moving or position-variable structure(s) located or partially located in the ROI. Further, the processing device 140 may determine the registration mask by setting values of pixels (or voxels) corresponding to structure(s) in the inclusion set as 1 and setting values of pixels (or voxels) corresponding to structure(s) in the exclusion set as 0 or values close to 0. In some embodiments, structures in the inclusion set may also be referred to as target structures and structures in the exclusion set may also be referred to as interference structures. In some embodiments, the identified structures may be expanded by a spatial margin. For example, the moving or position-variable structures may be expanded by a specific spatial margin to accommodate possible motion.

In some embodiments, the processing device 140 may generate an intermediate image by removing image information outside the ROI from the reference image and determine the registration mask associated with the ROI based on the intermediate image. For example, the processing device 140 may determine the intermediate image by setting values of pixels (or voxels) outside the ROI in the reference image as 0 or values close to 0. Further, the processing device 140 may determine the registration mask by setting values of pixels (or voxels) in the ROI in the intermediate image as 1.

In some embodiments, the processing device 140 may determine the registration mask based on a preliminary mask and an auxiliary mask. The preliminary mask may be a mask including the ROI and the auxiliary mask may be a mask including one or more interference structures (e.g., a moving organ, a moving tissue) at least partially located in the ROI. More descriptions regarding the determination of the registration mask may be found elsewhere in the present disclosure (e.g., FIG. 6 and the description thereof).

In 530, the processing device 140 (e.g., the obtaining module 410) may obtain a target image of the object. The target image may include the target volume. Each pixel (or voxel) in the target image may correspond to one pixel (or voxel) in the reference image. As used herein, two corresponding pixels (or voxels) in the reference image and the target image may correspond to a same or a similar physical portion or position of the object.

In some embodiments, the processing device 140 may obtain the target image from the medical device 110 (e.g., the imaging device 111) or the storage device 150. For example, the imaging device 111 may transmit acquired target imaging data (e.g., projection data) of the object to the storage device 150 for storage. The processing device 140 may obtain the target imaging data from the storage device 150 and generate the target image based on the target imaging data. As another example, the processing device 140 may obtain the target image from the storage device 150 directly.

In some embodiments, similar to the reference image, the target image may be a 2D image, a 3D image, a 4D image, etc. In some embodiments, the target image may be a measured image during the radiation treatment. For example, the target image may be a 3D scan image (e.g., a 3D CT image) of the object which is determined based on scanning data of the object obtained during the radiation treatment. As another example, the target image may be a 2D scan image (e.g., an X-ray image) of the object which is determined based on scanning data of the object obtained during the radiation treatment.

In some embodiments, the target image and the reference image may be generated at different time points. For example, as described above, the reference image (e.g., a planning image) may be generated before the radiation treatment and the target image (e.g., an X-ray image) may be generated during the radiation treatment. As another example, both the reference image and the target image may be generated at different time points before the radiation treatment, for example, the reference image may be generated earlier than the target image. In some embodiments, the target image and the reference image may be generated based on scanning data obtained by different imaging devices, that is, the modality of the reference image and that of the target image may be different. For example, the reference image may be a CT image generated based on a CT scan before the radiation treatment; the target image may be an X-ray image generated based on an X-ray scan during the radiation treatment. As another example, the reference image may be a PET image generated based on a PET scan; the target image may be an MRI image generated based on an MRI scan. Alternatively, the modality of the reference image and that of the target image may be different or the same. For example, both the reference image and the target image may be CT images, which are acquired by a same CT device before the radiation treatment and during the radiation treatment respectively.

In some embodiments, the target image and the reference image may correspond to a same respiratory phase of the object. For example, a respiratory cycle of the object may include an inspiratory phase, a breathless phase (i.e., a phase in which the breath is held), and an expiratory phase. Accordingly, both the target image and the reference image may correspond to the breathless phase. In some embodiments, the reference image and the target image may correspond to a same interval of the respiratory cycle. For example, both the reference image and the target image may be an average image of a plurality of images acquired within a predetermined interval of the respiratory cycle.

In 540, the processing device 140 (e.g., the image registration module 430) may perform an image registration on the reference image and the target image based on the registration mask.

In some embodiments, the image registration may include a 3D-3D registration, a 3D-2D registration, a 2D-2D registration, or the like, or a combination thereof. In some embodiments, when the dimensions of the reference image, the target image, and the registration mask are the same, the processing device 140 may apply the registration mask on the reference image and the target image directly to perform the image registration.

In some embodiments, when the dimensions of the reference image, the target image, and/or the registration mask are different, the processing device 140 may process the reference image, the target image, and/or the registration mask to a same dimension. Then the processing device 140 may perform the image registration based on the processed images. For example, when the reference image and the registration mask are 3D images, and the target image is a 2D image, the processing device 140 may generate a 2D reference image and a 2D registration mask by projecting the 3D reference image and the 3D registration mask onto a predetermined plane. Then the processing device 140 may perform the image registration on the 2D reference image and the 2D target image based on the 2D registration mask. As another example, when the reference image and the registration mask are 3D images, and the target image is a 2D image, the processing device 140 may generate a 3D target image by reconstructing the 2D target image. Then the processing device 140 may perform the image registration on the 3D reference image and the 3D target image based on the 3D registration mask. As a further example, when the reference image and the registration mask are 2D images, and the target image is a 3D image, the processing device 140 may generate a 2D target image by projecting the 3D target image onto a predetermined plane. Then the processing device 140 may perform the image registration on the 2D reference image and the 2D target image based on the 2D registration mask.

In some embodiments, the processing device 140 may perform the image registration using an image registration technique. In some embodiments, the image registration technique may include a grayscale-based technique, a transform-domain based technique, a feature-based technique, or the like, or any combination thereof. In some embodiments, the processing device 140 may determine a masked reference image and a masked target image by applying the registration mask on the reference image and the target image, respectively. Further, the processing device 140 may perform the image registration on the masked reference image and the masked target image. In some embodiments, the processing device 140 may determine one or more shift parameters based on the masked reference image and the masked target image. More descriptions regarding the image registration between the reference image and the target image based on the registration mask may be found elsewhere in the present disclosure (e.g., FIG. 7 and the description thereof).

It should be noted that the above description regarding the process 500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be omitted and/or one or more additional operations may be added. For example, the process 500 may further include an operation in which the processing device 140 may drive the table 113 of the medical system 100 to move according to the one or more shift parameters. As another example, the process 500 may further include an operation in which the processing device 140 may transmit the one or more shift parameters to a display of a terminal device (e.g., the terminal device 130) of a user (e.g., a doctor). Then the user may move the table 113 of the medical system 100 manually according to the one or more shift parameters.

FIG. 6 is a flowchart illustrating an exemplary process for determining a registration mask according to some embodiments of the present disclosure. In some embodiments, process 600 may be implemented as a set of instructions (e.g., an application) stored in the storage device 150, storage 220, or storage 390. The processing device 140, the processor 210, and/or the CPU 340 may execute the set of instructions, and when executing the instructions, the processing device 140, the processor 210, and/or the CPU 340 may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting. In some embodiments, operation 520 may be performed based on the process 600.

In 610, the processing device 140 (e.g., the mask determination module 420) may generate an intermediate image by removing image information outside the ROI from the reference image. For example, the processing device 140 may set values of reference pixels (or voxels) outside the ROI of the reference image as 0 or values close to 0. As a result, the intermediate image only includes image information of the ROI. As an additional example, pixel (or voxel) values that are to be excluded as information available for registration may be assigned a special value, such as NaN (not a number, such as in the IEEE 754 floating point number encoding standard) to indicate that the values are not to be considered.

In 620, the processing device 140 (e.g., the mask determination module 420) may determine a preliminary mask including the ROI based on the intermediate image. As used herein, the preliminary mask may be used to identify or position the ROI. For example, the processing device 140 may determine the preliminary mask by setting values of pixels (or voxels) corresponding to the ROI in the intermediate image as 1. Accordingly, the preliminary mask may be used to extract or distinguish image information of the ROI from the reference image.

In some embodiments, the dimension of the preliminary mask may be the same as the dimension of the intermediate image (or the reference image). For example, when the intermediate image (or the reference image) is a 3D image, the preliminary mask may be a 3D mask. In some embodiments, the dimension of the preliminary mask may be different from the dimension of the intermediate image (or the reference image).

In some embodiments, before determining the preliminary mask, the processing device 140 may perform a preprocessing operation on the intermediate image. In some embodiments, the preprocessing operation may include a filtering operation, a smoothing operation, a denoising operation, or the like, or any combination thereof. The processing device 140 may determine the preliminary mask based on the processed intermediate image. For example, the processing device 140 may determine a smoothed intermediate image by performing the smoothing operation on pixels (or voxels) with values exceeding a threshold in the intermediate image. Then the processing device 140 may determine the preliminary mask based on the smoothed intermediate image. The threshold may be set by a user or according to a default setting of the medical system 100 or may be adjustable under different situations. As another example, the processing device 140 may determine a filtered intermediate image by performing a filtering operation on the intermediate image, such that artifacts or noises can be reduced. Then the processing device 140 may determine the preliminary mask based on the filtered intermediate image.

In 630, the processing device 140 (e.g., the mask determination module 420) may identify one or more interference structures at least partially located in the ROI in the reference image.

As used herein, an interference structure refers to a structure that may affect the registration accuracy and/or stability between the reference image and a target image. For example, a moving structure or a position-variable structure due to a physiological movement (e.g., a respiratory movement, a cardiac movement, an artery pulsation) may be regarded as the interference structure since registration between medical images is often sensitive to the motion of organs or tissues. In some embodiments, the processing device 140 may expand the interference structure(s) by a spatial margin to accommodate possible motion of the interference structure(s).

In some embodiments, the one or more interference structures may include one or more moving organs or tissues, such as a heart, a lung (e.g., a left lung, a right lung), a diaphragm, a bladder, a rectum, or the like, or a portion thereof. In some embodiments, for different treatment purposes, the interference structure(s) may be different. For example, for a breast treatment, the one or more interference structures may include the left lung, the right lung, the heart, the diaphragm, or the like, or any combination thereof. As another example, for an abdominal treatment, the one or more interference structures may include moving parts of the alimentary canal, which have variable contents (e.g., a rectum) and/or contain a variable amount of gas. As a further example, for an abdominal treatment, the one or more interference structures may include the bladder which contains variable amounts of fluid.

In some embodiments, when the reference image is a DRR generated by projecting a 3D scan image onto an image plane, the one or more interference structures may be identified in the 3D scan image other than the reference image and may be projected onto the image plane using a projection geometry (which may be similar to that used to generate the reference image (i.e., the DRR image)). In some embodiments, for the projection operation, the processing device 140 may perform one or more operations including using a same energy spectrum as the actual imaging beam, modeling beam scatter or alternatively compensating the DRR for beam scatter, modeling a detector response function (e.g., an energy deposition response, a spatial response) of the detector used to acquire the DRR, or the like, or any combination thereof.

In some embodiments, the processing device 140 may identify the one or more interference structures based on structure types and/or structure labels (or structure identifiers). For example, the processing device 140 may identify the one or more interference structures based on a plurality of structure types and/or structure labels stored in a Radiation Treatment Structure Set (RTSS). In some other embodiments, the reference image may be generated according to a 4D imaging manner (which contains time information during imaging) and/or a cine imaging manner, that is, the reference image (or a cine reference image) can reflect time information, accordingly, the processing device 140 may identify the one or more interference structures based on the time information associated with the reference image. For example, a moving structure or a position-variable structure may occur in different time bins and can be identified based on the time information associated with the reference image (or the cine reference image). Specifically, the moving structure or the position-variable structure may be identified based on information that each structure changes over time. For example, the processing device 140 may determine a structure whose characteristic (e.g., position, shape, size, etc.) changes over time is the moving structure or position-variable structure.

In some embodiments, the processing device 140 may identify the one or more interference structures from a target image generated during treatment of the object in a manner similar to identifying interference structures from the reference image. For example, the target image may be generated according to a 4D imaging manner (which contains time information during imaging) and/or a cine imaging manner. The processing device 140 may identify the one or more interference structures based on time information associated with the target image.

In 640, the processing device 140 (e.g., the mask determination module 420) may determine an auxiliary mask including the one or more interference structures. As used herein, similar to the preliminary mask, the auxiliary mask may be used to identify or position the one or more interference structures. For example, the processing device 140 may determine the auxiliary mask by setting values of pixels (or voxels) in the one or more interference structures as 0 or values close to 0 and setting values of pixels (or voxels) outside the one or more interference structures as 1. As another example, the processing device 140 may determine the auxiliary mask by setting values of pixels (or voxels) in the one or more interference structures as 1 and setting values of pixels (or voxels) outside the one or more interference structures as 0 or values close to 0.

In 650, the processing device 140 (e.g., the mask determination module 420) may determine a registration mask associated with the ROI based on the preliminary mask and the auxiliary mask.

In some embodiments, the processing device 140 may determine the registration mask by combining the preliminary mask and the auxiliary mask. For example, if the values of pixels (or voxels) in the one or more interference structures are set as 0 in the auxiliary mask, the processing device 140 may determine the registration mask by multiplying the preliminary mask and the auxiliary mask. As another example, if the values of pixels (or voxels) in the one or more interference structures are set as 1 in the auxiliary mask, the processing device 140 may determine the registration mask by subtracting the auxiliary mask from the preliminary mask. Accordingly, during the image registration, only structures in the ROI except for interference structure(s) are considered, which can improve the image registration accuracy and remove or reduce the influence of the interference structure(s).

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be omitted and/or one or more additional operations may be added. For example, operation 630 and operation 640 may be combined as a single operation in which the processing device 140 may identify the one or more interference structures and determine the auxiliary mask based on the one or more interference structures.

FIG. 7 is a flowchart illustrating an exemplary process for registering a reference image with a target image based on a registration mask according to some embodiments of the present disclosure. In some embodiments, process 700 may be implemented as a set of instructions (e.g., an application) stored in the storage device 150, storage 220, or storage 390. The processing device 140, the processor 210, and/or the CPU 340 may execute the set of instructions, and when executing the instructions, the processing device 140, the processor 210, and/or the CPU 340 may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting. In some embodiments, operation 540 may be performed based on process 700.

In 710, the processing device 140 (e.g., the image registration module 430) may determine a masked reference image by applying a registration mask on a reference image. For example, the processing device 140 may determine the masked reference image by multiplying the registration mask and the reference image. Specifically, the processing device 140 may determine the masked reference image by multiplying a value of each pixel (or voxel) in the reference image and a value of a corresponding pixel (or voxel) in the registration mask. As described elsewhere in the present disclosure, since the registration mask only includes information corresponding to the ROI without interference structure(s), the masked reference image may only include image information of the ROI without interference structure(s).

In 720, the processing device 140 (e.g., the image registration module 430) may determine a masked target image by applying the registration mask on a target image. The processing device 140 may determine the masked target image in a manner similar to the determination of the masked reference image.

In 730, for each of one or more target regions in the masked target image, the processing device 140 (e.g., the image registration module 430) may determine a similarity value between the target region and a corresponding reference region in the masked reference image. The similarity value may indicate a spatial transformation between the target region in the masked target image and the corresponding reference region in the masked reference image.

In some embodiments, the processing device 140 may determine the similarity value between the target region and the corresponding reference region based on characteristics (e.g., a gray value, a size, a contrast, a resolution) of the target region and the corresponding reference region. For example, it is assumed that both the target region and the reference region correspond to a pixel (or voxel), the processing device 140 may determine the similarity value based on a difference between a characteristic (e.g., a gray value) of a target pixel (or voxel) of the masked target image and a characteristic (e.g., a gray value) of a reference pixel or (voxel) of the masked reference image. As another example, it is assumed that both the target region and the reference region correspond to an "area," the processing device 140 may determine a weighted target characteristic of the target region by weighting pixels (or voxels) in the target region and a weighted reference characteristic of the reference region by weighting pixels (or voxels) in the reference region. Then the processing device 140 may determine the similarity value based on a difference between the weighted target characteristic of the target region and the weighted reference characteristic of the reference region.

In 740, the processing device 140 (e.g., the image registration module 430) may determine one or more shift parameters based on one or more similarity values corresponding to the one or more target regions. As used herein, the one or more shift parameters may be used to make the masked target image (or the target image) match the masked reference image (or the reference image).

For example, when the reference image is a planning image (e.g., a CT DRR) and the target image is a treatment image (e.g., an X-ray image) during a radiation treatment, a position of one or more components of the medical system

100 (e.g., the table 113, the gantry of the treatment device 112) may be adjusted based on the one or more shift parameters (e.g., a translation parameter, a rotation parameter) so that the radiation treatment may be accurately delivered to the target volume of the object. As another example, when the reference image is a PET image and the target image is an MRI image, the processing device 140 may determine a fused image by fusing the PET image and the MRI image based on the one or more shift parameters so that anatomical information and/or functional information related to the object with improved accuracy for diagnosis and/or treatment purposes may be provided by the fused image.

In some embodiments, the processing device 140 may determine a similarity map based on the similarity values. The processing device 140 may determine the one or more shift parameters based on the similarity map.

In some embodiments, the processing device 140 may determine the one or more shift parameters based on a registration cost function which may be formed as a similarity metric (e.g., a mean squared error (MSE) metric, a mutual information (MI) metric, a normalized cross correlation (NCC) metric) representing the similarity between the masked target image and the masked reference image. For example, the processing device 140 may determine one or more initial shift parameters based on one or more initial similarity values corresponding to the one or more target regions. Then the processing device 140 may (iteratively) optimize the registration cost function using an optimization algorithm by (iteratively) updating the one or more initial shift parameters until updated one or more similarity values satisfy a preset condition. In some embodiments, the optimization algorithm may include a Powell's optimization algorithm (POA), a simulated annealing algorithm, a genetic optimization algorithm, an exhaustive search algorithm, a regular step gradient descent algorithm (RSGDA), a Fruit-fly optimization algorithm (FOA), a bacterial chemotaxis fruit-fly optimization algorithm (BCFOA), or the like, or any combination thereof.

It should be noted that the above description regarding the process 700 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

EXAMPLES

The following examples are provided for illustration purposes and are not intended to limit the scope of the present disclosure.

Figure 8A:
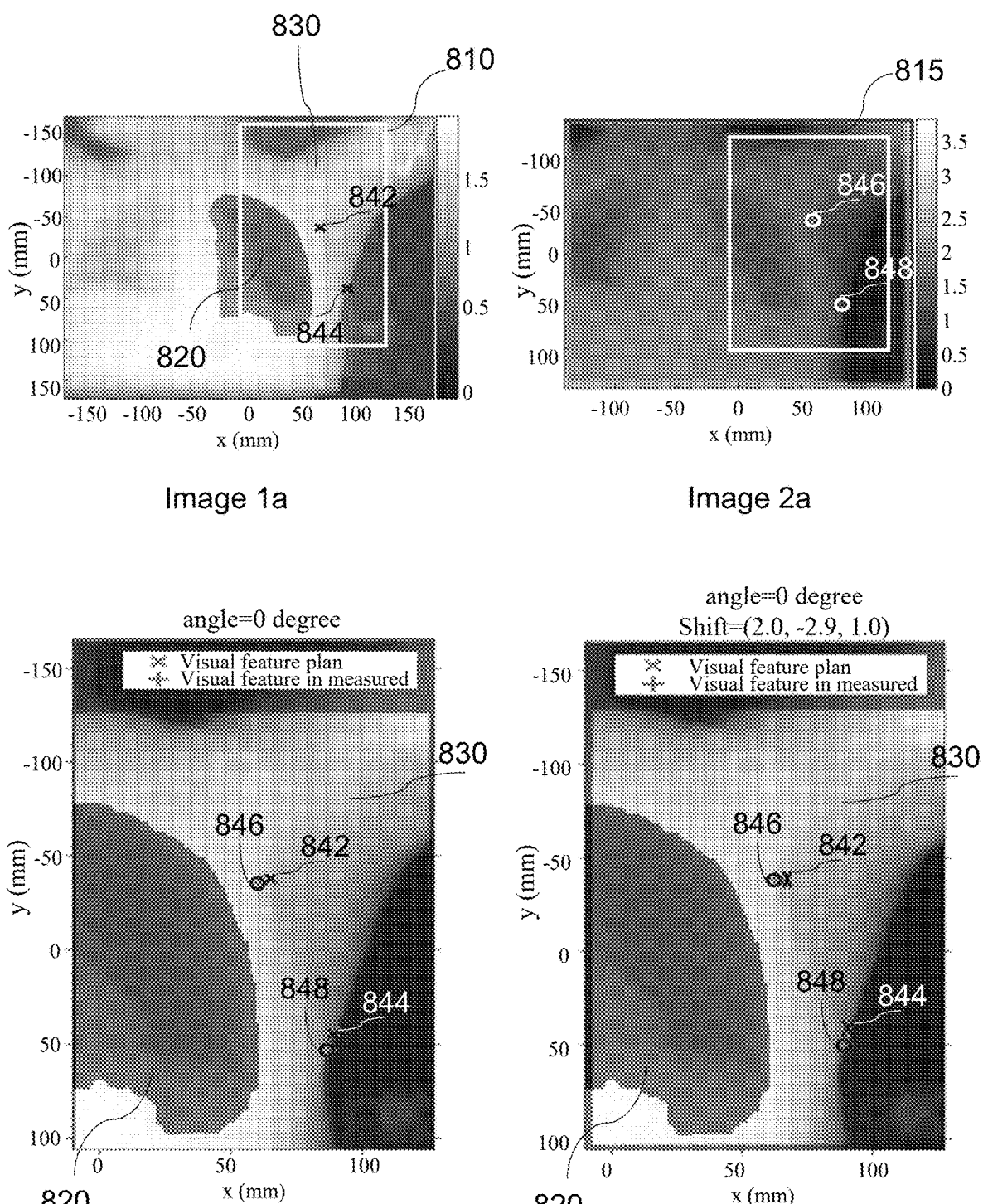
FIG. 8A illustrates an exemplary image registration process between a planning image and a treatment image based on a registration mask during a breast-area treatment according to some embodiments of the present disclosure.
Figure 8B:
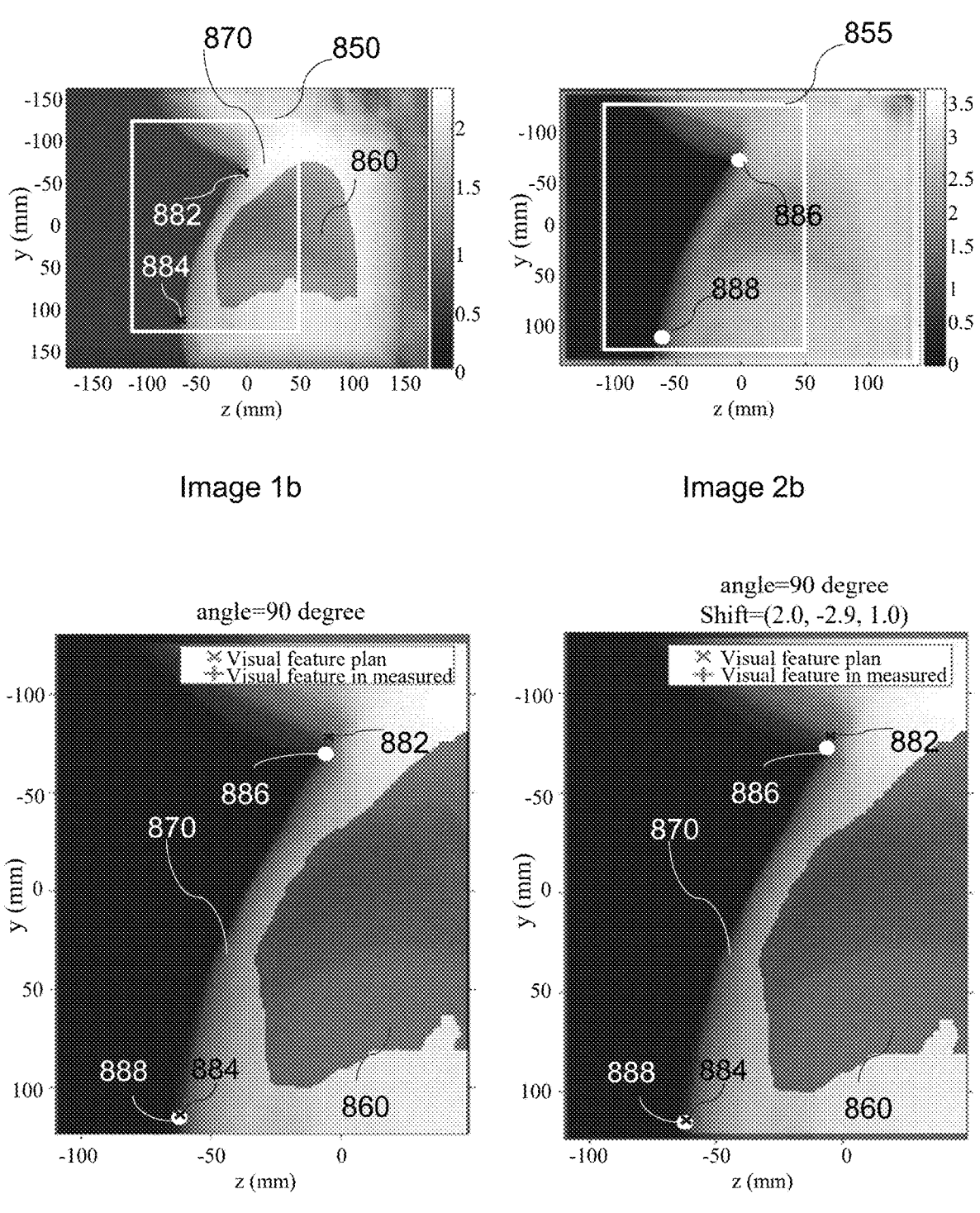
FIG. 8B illustrates an exemplary image registration process between a planning image and a treatment image based on a registration mask during the breast-area treatment according to some embodiments of the present disclosure.

FIG. 8A illustrates an exemplary image registration process between a planning image and a treatment image based on a registration mask during a breast-area treatment according to some embodiments of the present disclosure. Images in FIG. 8A correspond to a zero-degree gantry position. FIG. 8B illustrates an exemplary image registration process between a planning image and a treatment image based on a registration mask during the breast-area treatment according to some embodiments of the present disclosure. Images in FIG. 8B correspond to a 90-degree gantry position. During the breast-area treatment, since the left lung and the lung-diaphragm move with the respiration of the patient, the left lung and the lung-diaphragm may be regarded as interference structures during the breast-area treatment. Accordingly, as described in connection with FIG. 6, a registration mask corresponding to an ROI of the breast-area with the interference structures removed may be generated.

As illustrated in FIG. 8A, image 1*a* is a first DRR (i.e., a reference image) of the patient generated at any time before the breast-area treatment. The first DRR may be generated based on a geometry calibration model of a beam spectrum, a detector response function, and a linac imaging system geometry calibration. The first DRR may be used as a first planning image. Image 2*a* is a first X-ray image (i.e., a target image) measured in real time during the breast-area treatment. The first X-ray image may be used as a first treatment image. Image 3*a* is a first visualized image determined by applying a first registration mask on the first DRR and the first X-ray image. Image 4*a* is a first registration image indicating a final registration result of the first DRR and the first X-ray image, that is, the first X-ray image is shifted based on the one or more shift parameters.

Further, a rectangular box 810 in the image 1*a* refers to a default ROI of the first DRR and a rectangular box 815 in the image 2*a* refers to a default ROI in the first X-ray image; a black portion 820 refers to a first auxiliary mask corresponding to the interference structure(s) (e.g., the left lung); a region 830 refers to a first preliminary mask including the ROI. Accordingly, the first registration mask is a mask determined by multiplying the first preliminary mask and the first auxiliary mask. That is, the interference structures are excluded from the ROI during the registration process. Marks 842, 844, 846, and 848 are manually or automatically identified features that are used for visual performance assessment.

Images in FIG. 8B are similar to images in FIG. 8A. For example, image 1*b* is a second DRR of the patient generated at any time before the breast-area treatment. The second DRR may be used as a second planning image. Image 2*b* is a second X-ray image of the patient measured in real time during the breast-area treatment. The second X-ray image may be used as a second treatment image. Image 3*b* is a second visualized image determined by applying a second registration mask on the second DRR and the second X-ray image. Image 4*b* is a second image indicating a final registration result of the second DRR and the second X-ray image, that is, the second X-ray image is shifted based on the one or more shift parameters.

Further, a rectangular box 850 in the image 1*b* refers to a default ROI of the second DRR and a rectangular box 855 in the image 2*b* refers to a default ROI in the second X-ray image; a black portion 860 refers to a second auxiliary mask corresponding to the interference structure(s) (e.g., the left lung); a region 870 refers to a second preliminary mask including the ROI. Accordingly, the second registration mask is a mask determined by multiplying the second preliminary mask and the second auxiliary mask. That is, the interference structures are excluded from the ROI during the registration process. Marks 882, 884, 886, and 888 are also manually or automatically identified features that are used for visual performance assessment.

In some embodiments, during the image registration process, the one or more shift parameters may be determined using a mean squared error (MSE) cost function. In some embodiments, an inclusion mask (also can be considered as the "registration mask") may be denotes as Equation (1) below:

$$I_v = R_v \backslash X_v, \qquad (1)$$

where $I_v$ denotes the inclusion mask; $R_v$ denotes the ROI (also can be considered as the "preliminary mask"); and $X_v$ denotes the exclusion mask (also can be considered as the "auxiliary mask").

In some embodiments, in the continuous space domain, a first mean squared error (MSE) cost function may be denoted as Equation (2) below:

$$\hat{s} = \underset{s}{\text{argmin}} \sum_{v=1}^{V} \frac{1}{|I_v|} \int_{x \in I_v} du_v (M_v(u_v - s) - F_v(u_v))^2, \qquad (2)$$

where s denotes the shift parameters, a vector of the shift parameters may be defined as $$s = [\, \delta_x \quad \delta_y \quad \delta_z \,]^T;$$

$u_v$ denotes an image coordinate; $M_v(u_v)$ denotes the X-ray image (e.g., the first X-ray image or the second X-ray image); $M_v(u_v - S)$ denotes a shifted (or transformed) X-ray image (e.g., a first shifted X-ray image or a second shifted X-ray image) determined based on the shift parameters; $F_v(u_v)$ denotes the DRR (e.g., the first DRR or the second DRR). Since the images in FIGS. 8A and 8B share one axis (y), the image coordinate correspond to the 0-degree gantry position may be defined as $$u_{0\ degree} = [\, x \quad y \,]^T$$

and the image coordinate correspond to the 90-degree gantry position may be defined as $$u_{90\ degree} = [\, z \quad y \,]^T.$$

Then the shift parameters may be determined by optimizing (e.g., minimizing) the first MSE cost function. In some embodiments, in order to provide more rapid convergence to the approximate solution, it may be useful to decouple the estimations at least at the start of optimization.

In some embodiments, in the discrete space domain, a second MSE cost function may be denoted as Equation (3) below:

$$\hat{s} = \underset{s}{\text{argmin}} \sum_{v=1}^{V} \frac{1}{|I_v|} \sum_{m,n \in I_v} (M_v[m - s_m^v, n - s_n^v] - F_v[m, n])^2, \qquad (3)$$

where s denotes the shift parameters, a vector of the shift parameters may be defined as $$s = [\, s_m^1 \quad s_n^1 \quad s_m^2 \,]^T,$$

wherein $$s_n^2 = s_n^1;$$

m and n denote image pixel indices;

$$s_m^y \text{ and } s_n^y$$

denote the respective pixel shifts which may be integers or fractions of a pixel. In the latter case, interpolation can be used to calculate the second MSE cost function. Alternatively, if subpixel resolution is desired, the images can be upsampled before the shifts optimization proceeds.

During the image registration in FIGS. 8A and 8B, an exhaustive search may be used where the cost functions are evaluated for all pixel shifts within a range of ±3.5 cm. As a result, the optimal shift parameters are found to be s=[1.95-2.93 0.977] mm. It should be noted that, these examples, for purposes of demonstration only, illustrate linear shift (translation) registration transforms. It is understood that affine and deformable registration (elastic) transforms may be similarly applied.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A system for image registration, comprising:

at least one storage device storing executable instructions, and at least one processor in communication with the at least one storage device, when executing the executable instructions, causing the system to perform operations including:

obtaining a reference image of an object, the reference image including a target volume;

determining a registration mask associated with a region of interest (ROI) based on the reference image, the ROI including at least a portion of the target volume, wherein the registration mask is configured to exclude at least a portion of one or more interference structures, and the at least a portion of the one or more interference structures locates in the ROI;

obtaining a target image of the object, the target image including the target volume; and performing an image registration on the reference image and the target image based on the registration mask.

2. The system of claim 1, wherein the determining the registration mask associated with the ROI based on the reference image includes:

generating an intermediate image by removing image information outside the ROI from the reference image; and determining the registration mask associated with the ROI based on the intermediate image.

3. The system of claim 2, wherein the determining the registration mask associated with the ROI based on the intermediate image includes:

performing a filtering operation on the intermediate image; and determining the registration mask associated with the ROI based on the filtered intermediate image.

4. The system of claim 1, wherein the determining the registration mask associated with the ROI based on the reference image includes:

determining a preliminary mask including the ROI based on the reference image;

identifying the one or more interference structures at least partially located in the ROI in the reference image;

determining an auxiliary mask including the one or more interference structures; and determining the registration mask associated with the ROI based on the preliminary mask and the auxiliary mask.

5. The system of claim 4, wherein the identifying the one or more interference structures at least partially located in the ROI in the reference image includes:

automatically segmenting the one or more interference structures from the reference image based on a preset rule.

6. The system of claim 5, wherein the preset rule includes at least one of a structure type, a structure label, or time information associated with the reference image.

7. The system of claim 4, wherein the one or more interference structures include at least one of a moving organ or a moving tissue.

8. The system of claim 7 where the moving organ or moving tissues are determined from cine reference images.

9. The system of claim 7 where the moving organ or moving tissues are determined from cine target images.

10. The system of claim 7 where the moving organ or moving tissues are determined from motion characteristics of organs or tissues identified in the target or reference images.

11. The system of claim 4, wherein the one or more interference structures include at least one of a heart, a lung, a diaphragm, a bladder, or a rectum.

12. The system of claim 4, wherein the determining the registration mask associated with the ROI based on the preliminary mask and the auxiliary mask includes:

determining the registration mask by combining the preliminary mask and the auxiliary mask.

13. The system of claim 4, wherein the determining the registration mask associated with the ROI based on the preliminary mask and the auxiliary mask includes:

determining the registration mask by multiplying the preliminary mask and the auxiliary mask.

14. The system of claim 1, wherein the performing the image registration on the reference image and the target image based on the registration mask includes:

determining a masked reference image by applying the registration mask on the reference image;

determining a masked target image by applying the registration mask on the target image; and determining one or more shift parameters based on the masked reference image and the masked target image.

15. The system of claim 14, wherein the determining the one or more shift parameters based on the masked reference image and the masked target image includes:

for each of one or more target regions in the masked target image, determining a similarity value between the target region and a corresponding reference region in the masked reference image; and determining the one or more shift parameters based on one or more similarity values corresponding to the one or more target regions.

16. The system of claim 1, wherein the reference image and the target image are acquired at a same respiratory phase.

17. The system of claim 16, wherein both the reference image and the target image are an average image of a plurality of images acquired within a predetermined interval of a respiratory cycle of the object.

18. A method for image registration, implemented on a computing device having at least one processor and at least one storage device, the method comprising:

obtaining a reference image of an object, the reference image including a target volume;

determining a registration mask associated with a region of interest (ROI) based on the reference image, the ROI including at least a portion of the target volume, wherein the registration mask excludes at least a portion of one or more interference structures, and the at least a portion of the one or more interference structures locates in the ROI;

obtaining a target image of the object, the target image including the target volume; and performing an image registration on the reference image and the target image based on the registration mask.

19. The method of claim 18, wherein the performing the image registration on the reference image and the target image based on the registration mask includes:

determining a masked reference image by applying the registration mask on the reference image;

determining a masked target image by applying the registration mask on the target image; and determining one or more shift parameters based on the masked reference image and the masked target image.

20. A non-transitory computer readable medium, comprising at least one set of instructions for image registration, wherein when executed by at least one processor of a computing device, the at least one set of instructions direct the at least one processor to perform operations including:

obtaining a reference image of an object, the reference image including a target volume;

determining a registration mask associated with a region of interest (ROI) based on the reference image, the ROI including at least a portion of the target volume, wherein the registration mask excludes at least a portion of one or more interference structures, and the at least a portion of the one or more interference structures locates in the ROI;

obtaining a target image of the object, the target image including the target volume; and performing an image registration on the reference image and the target image based on the registration mask.

\* \* \* \* \*